United States Patent
Nicolau et al.

(10) Patent No.: US 12,290,510 B2
(45) Date of Patent: May 6, 2025

(54) POLYVALENT DERIVATIVES OF EMOXYPINE

(71) Applicant: Riesner Verwaltungs GMBH, Düsseldorf (DE)

(72) Inventors: Claude Nicolau, Boston, MA (US); Jean-Marie Lehn, Boston, MA (US); Renald Thinard, Boston, MA (US); Youssef Atoini, Boston, MA (US)

(73) Assignee: Riesner Verwaltungs GMBH, Düsseldorf (DE)

( * ) Notice: Subject to any disclaimer, the term of this patent is extended or adjusted under 35 U.S.C. 154(b) by 868 days.

(21) Appl. No.: 17/427,395

(22) PCT Filed: Feb. 7, 2020

(86) PCT No.: PCT/US2020/017192
§ 371 (c)(1),
(2) Date: Jul. 30, 2021

(87) PCT Pub. No.: WO2020/163704
PCT Pub. Date: Aug. 13, 2020

(65) Prior Publication Data
US 2022/0096451 A1 Mar. 31, 2022

Related U.S. Application Data

(60) Provisional application No. 62/802,323, filed on Feb. 7, 2019.

(51) Int. Cl.
*A61K 31/444* (2006.01)
*A61P 25/28* (2006.01)

(52) U.S. Cl.
CPC ............ *A61K 31/444* (2013.01); *A61P 25/28* (2018.01)

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |

(Continued)

FOREIGN PATENT DOCUMENTS

| | | |
|---|---|---|
| RU | 2 674 286 C1 | 3/2018 |
| WO | WO 2013/062762 A1 | 5/2013 |

(Continued)

OTHER PUBLICATIONS

Payne et al. "Neutral and cationic multinuclear half-sandwich rhodium and iridium complexes coordinated to poly(propyleneimine) dendritic scaffolds: Synthesis and cytotoxicity". Journal of Organometallic Chemistry. 729:20-27 (Year: 2013).*

(Continued)

*Primary Examiner* — Jeffrey S Lundgren
*Assistant Examiner* — Anthony Joseph Seitz
(74) *Attorney, Agent, or Firm* — Morgan, Lewis & Bockius LLP

(57) ABSTRACT

Use of polyvalent emoxypine derivatives or related compounds in the treatment or prevention of, inter alia, Parkinson's Disease are described.

10 Claims, 4 Drawing Sheets

Specification includes a Sequence Listing.

A

B

(56) References Cited

U.S. PATENT DOCUMENTS

| | | | |
|---|---|---|---|
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,556 | A | 3/1998 | Schrier et al. |
| 2011/0009619 | A1 | 1/2011 | Kimura et al. |
| 2014/0038980 | A1* | 2/2014 | Snow .......... C07D 213/85 514/277 |
| 2015/0126464 | A1 | 5/2015 | Tohda |

FOREIGN PATENT DOCUMENTS

| | | |
|---|---|---|
| WO | WO 2015/012780 A1 | 1/2015 |
| WO | WO 2015/023244 A1 | 2/2015 |
| WO | WO 2017/120012 A1 | 7/2017 |
| WO | WO 2019/074898 A1 | 4/2019 |
| WO | WO 2019/172737 A1 | 9/2019 |
| WO | WO 2020/191502 A1 | 10/2020 |

OTHER PUBLICATIONS

Smith et al. "The synthesis and catalytic activity of a first-generation poly(propylene imine) pyridylimine palladium matalodendrimer". Journal of Organometallic Chemistry. 673:111-115. (Year: 2003).*

Journal of Organometallic Chemistry, 729:20-27 (2013) (Year: 2013).*

Journal of Organometallic Chemistry, 673:111-115 (2003) (Year: 2003).*

Campbell, et al., "Complex Systems from Simple Building Blocks via Subcomponent Self-Assembly," Synlett, Retrieved from the Internet: https://www.academia.edu/5067091/Complex_Systems_from_Simple_Building_Blocks_via_Sub component_Self-Assembly, 14 pages, 2008.

International Search Report & Written Opinion, PCT Application No. PCT/US20/17192, dated Apr. 30, 2020, 11 pages.

Pubchem, Substance Record for SID 273458142., retrieved from the Internet: https://pubchem.nobi.nlm.nih.gov/substance/273458142, Dec. 18, 2015.

V.G. Kucherianu, "Mexidol potentiates antiparkinsonian effect of L-DOPA on the (1-Methyl-4-Phenyl-1,2,3,6 Tetrahydropyridine)-induced parkinsonism in mice", 2001, Department of Nervous System Patholoy, vol. 64, No. 1, pp. 22-25, http://www.ncbi.nlm.nih.gov/pubmed/11544797. Abstract.

Makletsova, et al., "The effect of antioxidants on in vivo and in vitro methemoglobin formation in erythrocytes of patients with parkinson's disease", 2016, Biochemistry (Moscov), Supplemental Series B: Biomedical Chemistry, vol. 10, No. 3, pp. 264-268.

Regino, et al., "N-Picolyl Derivatives of Kemp's Triamine as Potential Antitumor Agents: A Preliminary Investigation", 2005, Journal of Medicinal Chemistry, vol. 48, No. 25, pp. 7993-7999.

Supplemental European Search Report for European Application No. EP 20 75 2865, dated Sep. 21, 2022.

Torti, et al., "Preliminary evaluation of the cytotoxicity of a series of tris-2-aminoethylamine (Tren) based hexadentate heterocyclic donor agents", 2005, Bioorganic & Medicinal Chemistry, vol. 13, pp. 5961-5967.

Goetz, et al., "Movement Disorder Society-Sponsored Revision of the Unified Parkinson's Disease Scale (MDS-UPDRS): Process, Format, and Clinimetric Testing Plan," Movement Disorders, vol. 22, No. 1, pp. 41-47, 2007.

Goetz, et al., "Movement Disorder Society-Sponsored Revision of the Unified Parkinson's Disease Scale (MDS-UPDRS): Scale Presentation and Clinimetric Testing Results," Movement Disorders, vol. 23, No. 15, pp. 2129-2170, 2008.

Gruber, "Synthesis of 3-Hydroxy-2-Alkylpyridines," Canadian Journal of Chemistry, vol. 31, pp. 564-568, 1953.

Loznikova, et al., "The Effects of Magnesium, Acetylsalicylic Acid, and Emoxypine on Platelet Aggregation," Biophysics, vol. 59, No. 6, pp. 900-903, 2014.

Volchegorskii, et al., "Anxiolytic and Antidepressant Actions of Emoxypine, Reamberin, and Mexidol in Experimental Diabetes Mellitus," Neuroscience and Behavioral Physiology, vol. 49, No. 1, pp. 136-141, Jan. 2019.

* cited by examiner

A

SEQUENCE LISTING

<160> NUMBER OF SEQ ID NOS: 1

<210> SEQ ID NO 1
<211> LENGTH: 116
<212> TYPE: PRT
<213> ORGANISM: Artificial Sequence
<220> FEATURE:
<223> OTHER INFORMATION: Synthetic polymer.

<400> SEQUENCE: 1

Ser Asn Cys Ala Met Asp Val Phe Met Lys Gly Leu Ser Lys Ala Lys
1               5                   10                  15

Glu Gly Val Val Ala Ala Ala Glu Lys Thr Lys Gln Gly Val Ala Glu
                20                  25                  30

Ala Ala Gly Lys Thr Lys Glu Gly Val Leu Tyr Val Gly Ser Lys Thr
            35                  40                  45

Lys Glu Gly Val Val His Gly Val Ala Thr Val Ala Glu Lys Thr Lys
    50                  55                  60

Glu Gln Val Thr Asn Val Gly Gly Ala Val Val Thr Gly Val Thr Ala
65                  70                  75                  80

Val Ala Gln Lys Thr Val Glu Gly Ala Gly Ser Ile Ala Ala Ala Thr
                85                  90                  95

Gly Phe Val Lys Lys Asp Gln Leu Gly Lys Glu Gly Tyr Gln Asp Tyr
                100                 105                 110

Glu Pro Glu Ala
            115

POLYVALENT DERIVATIVES OF EMOXYPINE

CROSS-REFERENCE TO RELATED APPLICATIONS

This application is a National Stage Entry of PCT/US20/17192, filed Feb. 7, 2020, which claims the benefit of U.S. Provisional Patent Application No. 62/802,323, filed Feb. 7, 2019; the entire contents of which are hereby incorporated by reference.

TECHNICAL FIELD

The present invention relates, in part, to treatments of synucleinopathies.

DESCRIPTION OF THE TEXT FILE SUBMITTED ELECTRONICALLY

This application contains a sequence listing. It has been submitted electronically via EFS-Web as an ASCII text file entitled "ALS-008PC_ST25". The sequence listing is 1,438 bytes in size, and was recorded on or about Feb. 7, 2020. The sequence listing is hereby incorporated by reference in its entirety.

BACKGROUND

Parkinsonism or Parkinsonian syndromes are a group of progressive, neurodegenerative disorders that can significantly impair one's quality of life. Notable features of these diseases are tremor at rest, rigidity, bradykinesia and postural instability. Parkinson's disease afflicts 4% of the population over 80 years old.

The pathophysiology of Parkinson's disease is characterized, in part, by a synucleinopathy characterized by the abnormal accumulation of alpha-synuclein protein into inclusions called Lewy bodies in the brain. The distribution of the Lewy bodies throughout the brain varies from one individual to another but is often directly associated with the expression and degree of the clinical symptoms.

As no biological test is available, diagnosis of Parkinson's disease is mainly based on observation of clinical symptoms. Postmortem confirmation is required for a definitive diagnosis. The most widely used treatment, especially at earlier stages, is the dopamine precursor, levodopa (L-DOPA). However, most of the drug is metabolized before to reach the blood brain barrier (BBB), causing a variety of side effects, including gastrointestinal effects (such as anorexia, nausea or vomiting), dyskinesia and psychiatric symptoms.

Parkinson's disease remains an incurable disease and no effective disease-modifying treatment has been discovered yet. Therefore, there remains a need for more effective therapies for diseases such as Parkinson's disease.

SUMMARY

The present invention provides, in one aspect, compounds and methods for treating or preventing a synucleinopathy, comprising administering an effective amount of a polyvalent derivative of emoxypine (e.g., poly-imino or poly-amido emoxypine derivatives) to a subject in need thereof, wherein the method comprises disaggregation of α-synuclein. In various embodiments, the synucleinopathy is a condition characterized by Lewy bodies, e.g., Parkinson's disease, dementia with Lewy bodies, and multiple system atrophy.

In various embodiments, the compound is a poly-imino or poly-amido emoxypine derivative, e.g., tri- or tetra-imino emoxypine.

In some embodiments, the poly-imino or poly-amido emoxypine derivative is a compound of Formula I:

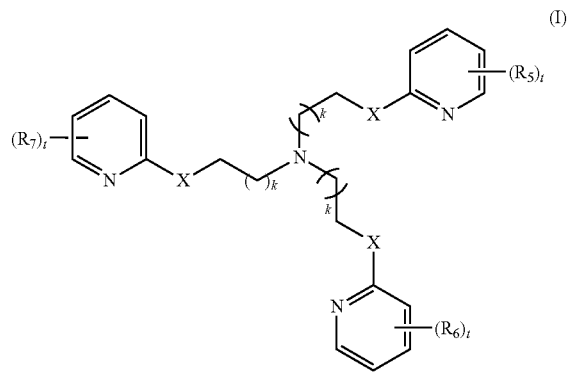

wherein:

X is —NH—C(=O)— or —CH(=N)—;

each $R_5$, $R_6$, or $R_7$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;

each t is independently 0, 1, 2, 3, 4, or 5;

each k is independently 0, 1, 2, 3, 4, 5, or 6.

In various embodiments, the compound is a tri imino-emoxypine (also known as "MHP-tren triimine").

In further embodiments, the compound is:

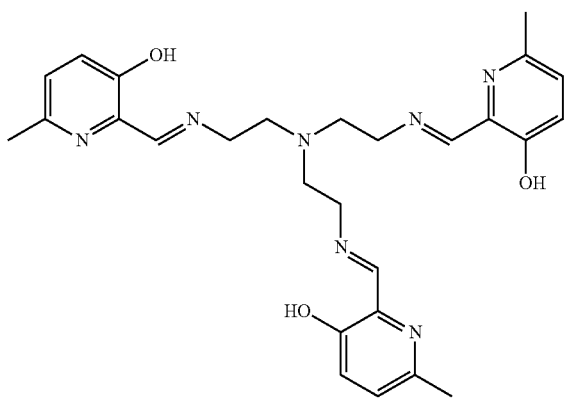 [SMILES: Cc1ccc(O)c(/C=N/CCN(CC/N=C/c2nc(C)ccc2O)CC/N=C/c2nc(C)ccc2O)n1]

In various embodiments, the compound is a tetra imino-emoxypine.

In some embodiments, the poly-imino or poly-amido emoxypine derivative is a compound of Formula II:

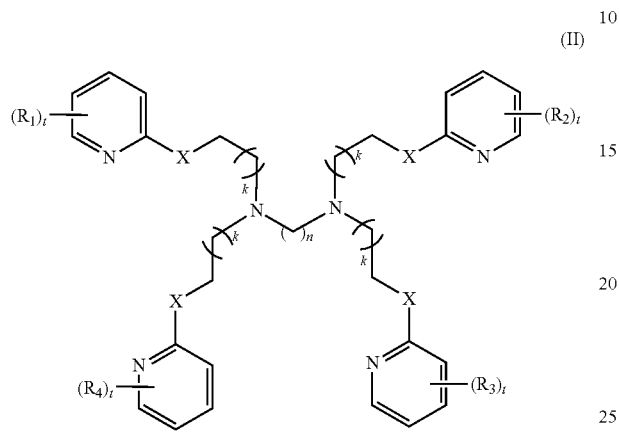

(II)

wherein:
X is —NH—C(=O)— or —CH(=N)—;
each $R_1$, $R_2$, $R_3$, or $R_4$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;
n is 2, 3, 4, 5, 6, 7, 8, 9, 10, 11, 12, 13, 14, or 15;
each t is independently 0, 1, 2, 3, 4, or 5;
each k is independently 0, 1, 2, 3, 4, 5, or 6.

In further embodiments, the compound is:

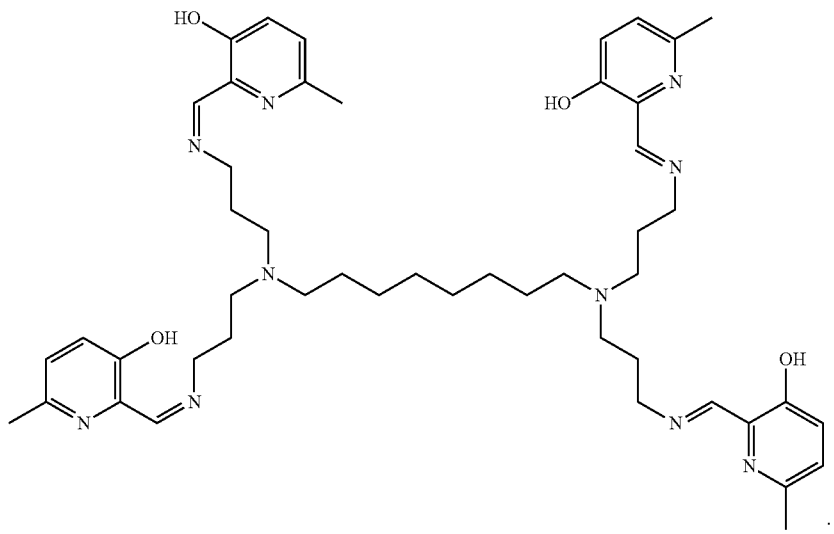 [SMILES: Cc1ccc(O)c(/C=N\CCCN(CCCCCCCCN(CCC/N=C/c2nc(C)ccc2O)CCC/N=C/c2nc(C)ccc2O)CCC/N=C\c2nc(C)ccc2O)n1]

In various embodiments, the compound is a poly-amido emoxypine derivative.

In further embodiments, the compound is:

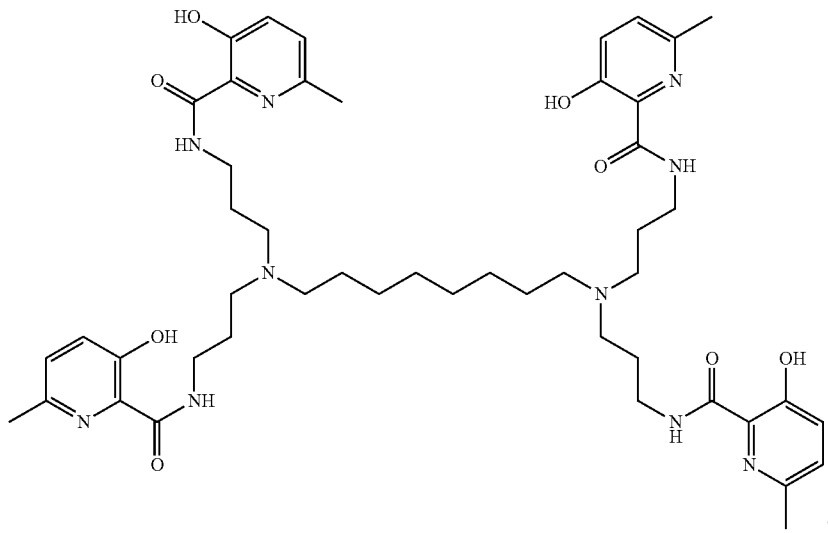 [SMILES: Cc1ccc(O)c(C(=O)NCCCN(CCCCCCCCN(CCCNC(=O)c2nc(C)ccc2O)CCCNC(=O)c2nc(C)ccc2O)CCCNC(=O)c2nc(C)ccc2O)n1]

In various embodiments, the method treats or prevents Parkinson's disease, selected from Idiopathic Parkinson's disease, Vascular parkinsonism, drug-induced parkinsonism, dementia with Lewy bodies, Inherited Parkinson's, Juvenile Parkinson's disease.

In various embodiments, the method provides about a 20%, or about a 30%, or about a 40%, or about a 50%, or about a 60%, or about a 70%, or about a 80%, or about a 85%, or about a 90%, or about a 95%, or about a 100% reduction in α-synuclein aggregation relative to an untreated subject. In various embodiments, the method provides for at least about a 20%, or about a 30%, or about a 40%, or about a 50%, or about a 60%, or about a 70%, or about a 75%, or about a 80%, or about a 85%, or about a 90%, or about a 95%, or about a 100% reduction in α-synuclein aggregation relative to an untreated subject.

In various embodiments, the method provided does not substantially dissolve aggregates of beta-amyloid.

DETAILED DESCRIPTION

Figure 1:
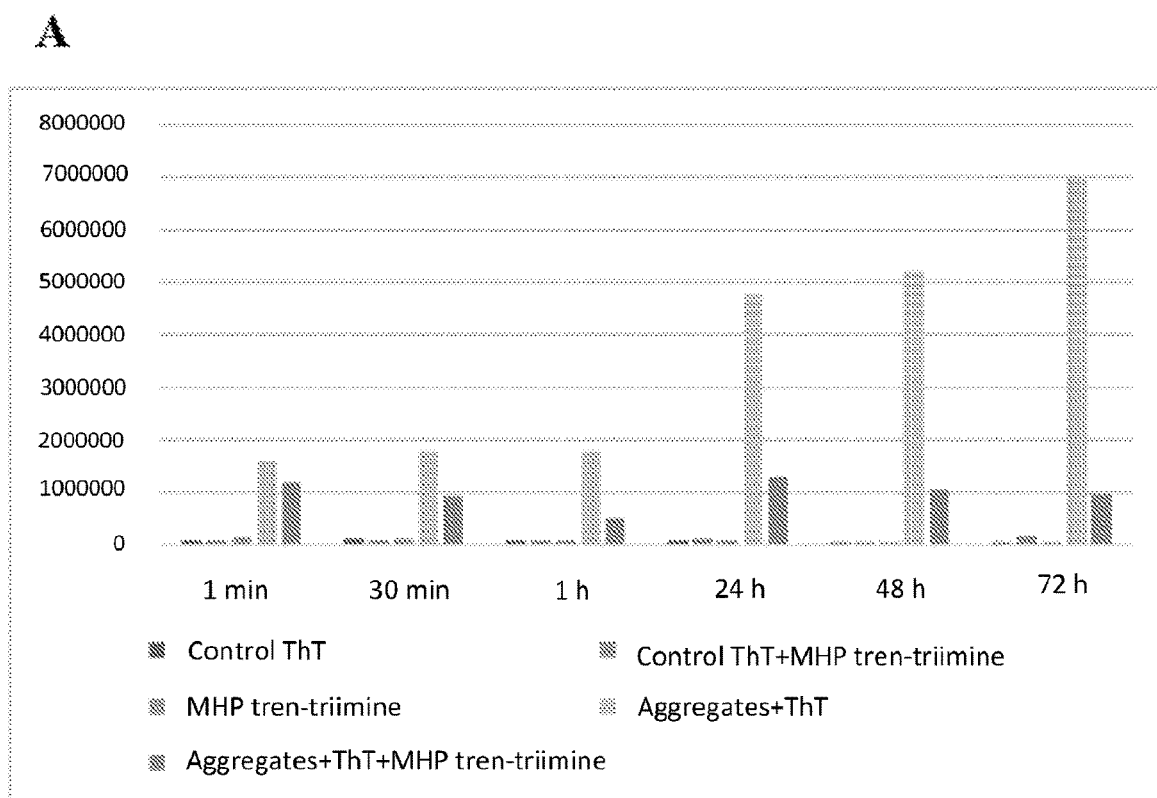
FIG. 1A depicts emission intensity of ThT at 482 nm (λexc=450 nm), in the presence of α-synuclein amyloids fibrils, with and without MHP-tren triimine (r70, light blue trace and yellow trace, respectively) from 1 minute to 3 days (72 h), where the bars from left to right in each set of histograms represents: control ThT; MHP tren-triimine; Aggregates+ThT+MHP tren-triimine; control ThT+MHP tren-triimine; and Aggregates+ThT, respectively.
FIG. 1B shows the percentage of α-synuclein amyloid fibrils left after addition of MHP-tren triimine (also known as tri imino-emoxypine) with r70, from 1 minute to 3 days (72 h), where the leftmost bar on the graph represents a sample without any MHP-tren triimine, i.e. with 100% of aggregates left.
Figure 1:
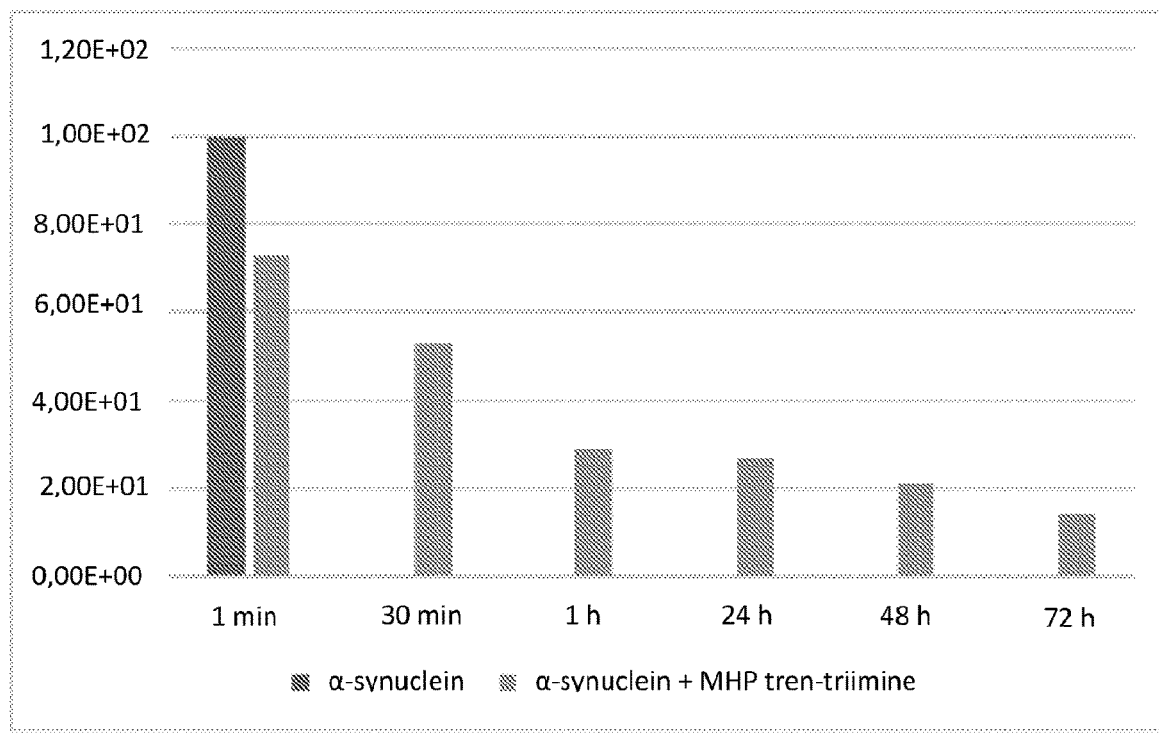

The present invention is based, in part, on the surprising discovery of a novel activity of polyvalent derivatives of emoxypine (including, but not limited to, tri imino-emoxypine (also known as "MHP-tren triimine"), tetra imino-emoxypine, and poly-amido emoxypine derivatives), specifically, in dissolving aggregates of alpha-synuclein (i.e., α-synuclein) but not aggregates of beta-amyloid (i.e., β-synuclein).

In some aspects, the present invention provides a method for treating or preventing a synucleinopathy, comprising administering an effective amount of a poly-imino or poly-amido derivative of emoxypine, including, but not limited to, a compound of Formula I or Formula II:

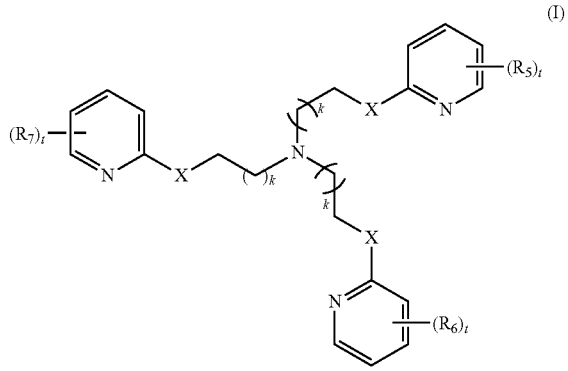

wherein:

X is —NH—C(=O)— or —CH(=N)—;

each $R_5$, $R_6$, or $R_7$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;

each t is independently 0, 1, 2, 3, 4, or 5;

each k is independently 0, 1, 2, 3, 4, 5, or 6, or (II)

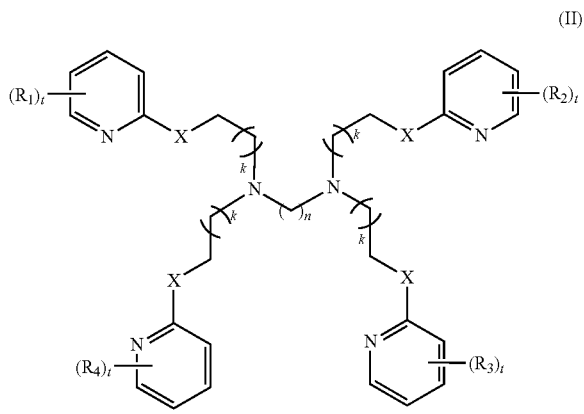

wherein:

X is —NH—C(=O)— or —CH(=N)—;

each $R_1$, $R_2$, $R_3$, or $R_4$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;

n is 2, 3, 4, 5, 6, 7, 8, 9, 10, 11, 12, 13, 14, or 15;

each t is independently 0, 1, 2, 3, 4, or 5;

each k is independently 0, 1, 2, 3, 4, 5, or 6, and wherein the method comprises disaggregation of α-synuclein.

In some aspects, the present invention provides a method for treating or preventing a synucleinopathy, comprising administering an effective amount of a polyvalent derivative of emoxypine, including, but not limited to, tri imino-emoxypine (also known as "MHP-tren triimine"), tetra imino-emoxypine, and poly-amido emoxypine derivatives, to a subject in need thereof, wherein the method comprises disaggregation of α-synuclein. In various embodiments, the synucleinopathy is a condition characterized by Lewy bodies, e.g., Parkinson's disease, dementia with Lewy bodies, and multiple system atrophy.

In various embodiments, the method provides about a 20%, or about a 30%, or about a 40%, or about a 50%, or about a 60%, or about a 70%, or about a 75%, or about a 80%, or about a 85%, or about a 90%, or about a 95%, or about a 100% reduction in α-synuclein aggregation relative to an untreated subject. In various embodiments, the method provides for at least about a 20%, or about a 30%, or about a 40%, or about a 50%, or about a 60%, or about a 70%, or about a 75%, or about a 80%, or about a 85%, or about a 90%, or about a 95%, or about a 100% reduction in α-synuclein aggregation relative to an untreated subject.

In various embodiments, the method provides does not substantially dissolve aggregates of beta-amyloid.

Neurodegenerative disorders, such as Parkinson, Huntington and Alzheimer diseases, fronto-temporal lobar degeneration (FTLD) and Amyotrophic Lateral Sclerosis (ALS) are associated with the accumulation of misfolded proteins both inside and outside of neuronal and glial cells in the central nervous system. These misfolded protein aggregates are pathological hallmarks of these diseases. The major component of these aggregates is characteristic for each neurodegenerative disease, e.g., alpha-synuclein for Parkinson.

Accordingly, in various embodiments, the present methods treat or prevent a synucleinopathy, e.g., Parkinson's disease by promoting the dissolution of aggregates of alpha-synuclein or preventing the accumulation of aggregates of alpha-synuclein, e.g., in the brain.

Lewy bodies are the hallmark of Parkinson's disease which is mainly composed of alpha-synuclein. Alpha-synuclein plays a role in the development of rare familial and more common sporadic cases of Parkinson's disease. In familial Parkinson's disease, the expression levels of alpha-synuclein gene is increased or an abnormal form of the protein is found which are toxic to brain cells and result in neuron dysfunction. Alpha-synuclein is the primary structural component of Lewy bodies, suggesting that protein aggregation plays a role in sporadic Parkinson's disease.

Alpha-synuclein is abundant in the human brain at the neurons tips in specialized structures called presynaptic terminals. Presynaptic terminals release chemical messengers, neurotransmitters, from synaptic vesicles. The release of neurotransmitters relays signals between neurons and is critical for normal brain function. So, alpha-synuclein is a presynaptic neuronal protein that is thought that its abnormal soluble oligomeric conformations, i.e. protofibrils, are the toxic species that mediate disruption of cellular homeostasis and neuronal death, through effects on various intracellular targets, including synaptic function. Furthermore, secreted alpha-synuclein may exert deleterious effects on neighboring cells, including seeding of aggregation, thus possibly contributing to disease propagation. In various embodiments, the present methods prevent or reduce the seeding of aggregation in a subject.

The human alpha-synuclein protein is made of 140 amino acids and is encoded by the SNCA gene. In some embodiments, the amino acid sequence of human alpha-synuclein is shown by SEQ ID NO.: 1:

SNCAMDVFMKGLSKAKEGVVAAAEKTKQGVAEAAGKTKEGVLYVGSKTK

EGVVHGVATVAEKTKEQVTNVGGAVVTGVTAVAQKTVEGAGSIAAATGF

VKKDQLGKEGYQDYEPEA.

In various embodiments, the present methods prevent or reduce the formation of Lewy bodies, e.g., in the brain.

Examples of Parkinsonism conditions that are treated or prevented by the present methods include Parkinson's disease, progressive supranuclear palsy, multiple system atrophy, cortical-basal ganglionic degeneration, diffuse Lewy body disease, Parkinson-dementia, X-linked dystonia-parkinsonism, and secondary Parkinsonism (resulting from environmental etiology, e.g., toxins, drugs, post encephalitic, brain tumors, head trauma, normal pressure hydrocephalus).

In various embodiments, the present methods prevent or reduce degeneration of dopaminergic neurons within the substantia nigra. In various embodiments, the present methods prevent or reduce tremor, hypokinesia (e.g., bradykinesia, akinesia, rigidity), postural instability, abnormal gait and swallowing disturbances. Non-motor symptoms include autonomic and neuropsychiatric disturbances such as anosmia, or sleep abnormalities.

As used herein, "treatment" includes the therapy, prevention, prophylaxis, retardation or reduction of symptoms provoked by or of the causes of Parkinsonism, e.g., Parkinson's disease. The term treatment also designates a retardation or delayed onset of tremor, a reduction of pain, a decrease or reduction of bradykinesia, akinesia, rigidity, postural instability, abnormal gait, anosmia, and/or sleep abnormalities, and/or an increase of survival. The term treatment includes in particular the control of disease progression and associated motor and non-motor symptoms. The term treatment, in various embodiments, particularly includes a protection against the toxicity caused by alpha-synuclein, or a reduction or retardation of this toxicity.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by 13C- or 14C-enriched carbons, are within the scope of this invention.

"Alkyl" refers to a straight or branched hydrocarbon chain radical consisting solely of carbon and hydrogen atoms, containing no unsaturation, having from one to ten carbon atoms (e.g., (C1-10)alkyl or C1-10 alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —ORa, —SRa, —OC(O)—Ra, —N(Ra)2, —C(O)Ra, C(O)ORa, —OC(O)N(Ra)2, —C(O)N(Ra)2, —N(Ra)C(O)ORa, —N(Ra)C(O)Ra, N(Ra)C(O)N(Ra)2, N(Ra)C(NRa)N(Ra)2, —N(Ra)S(O)tRa (where t is 1 or 2), —S(O)tORa (where t is 1 or 2), S(O)tN(Ra)2 (where t is 1 or 2), or PO3(Ra)2 where each Ra is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxy" or "alkoxyl" refers to the group —O-alkyl or -alkylene-O-alkyl, including from 1 to 8 carbon atoms of a straight, branched, cyclic configuration and combinations thereof attached to the parent structure. Examples include, but are not limited to, methoxy, ethoxy, propoxy, isopropoxy, cyclopropyloxy, cyclohexyloxy, and —CH2CH2-O—CH3. "Lower alkoxy" refers to alkoxy groups containing one to six carbons.

The term "aryl" or "Ar" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkyl" includes optionally substituted alkyl radicals and which have one or more skeletal chain atoms selected from an atom other than carbon, e.g., oxygen, nitrogen, sulfur, phosphorus or combinations thereof. A numerical range may be given—e.g., C1-C4 heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —ORa, —SRa, —OC(O)—Ra, —N(Ra)2, C(O)Ra, C(O)ORa, —OC(O)N(Ra)2, —C(O)N(Ra)2, —N(Ra)C(O)ORa, —N(Ra)C(O)Ra, N(Ra)C(O)N(Ra)2, N(Ra)C(NRa)N(Ra)2, —N(Ra)S(O)tRa (where t is 1 or 2), —S(O)tORa (where t is 1 or 2), S(O)tN(Ra)2 (where t is 1 or 2), or PO3(Ra)2, where each Ra is independently hydrogen, alkyl, fluoroalkyl, carbocyclyl, carbocyclylalkyl, aryl, heterocycloalkyl, heterocycloalkylalkyl, heteroaryl or heteroarylalkyl.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "cycloalkyl" includes saturated carbocyclic groups. Preferred cycloalkyl groups include C3-C6 rings. More preferred compounds include, cyclopentyl, cyclopropyl, and cyclohexyl.

The term "heterocyclyl" (or "heterocyclo") embraces saturated, partially saturated and unsaturated heteroatom-containing ring radicals, where the heteroatoms may be selected from nitrogen, sulfur and oxygen. It does not include rings containing —O—O—, —O—S— or —S—S— portions. The "heterocyclyl" group may have 1 to 4 substituents such as hydroxyl, Boc, halo, haloalkyl, cyano, lower alkyl, lower aralkyl, oxo, lower alkoxy, amino and lower alkylamino.

"Halo", "halide", or, "halogen" is intended to mean fluoro, chloro, bromo or iodo.

"Heteroaryl" or "heteroaromatic" or "HetAr" refers to a 5- to 18-membered aromatic radical (e.g., C5-C13 heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —ORa, —SRa, —OC(O)—Ra, —N(Ra)2, C(O)Ra, C(O)ORa, —OC(O)N(Ra)2, —C(O)N(Ra)2, —N(Ra)C(O)ORa, —N(Ra)C(O)Ra, N(Ra)C(O)N(Ra)2, N(Ra)C(NRa)N(Ra)2, —N(Ra)S(O)tRa (where t is 1 or 2), —S(O)tORa (where t is 1 or 2), S(O)tN(Ra)2 (where t is 1 or 2), or PO3(Ra)2, where each Ra is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

As used herein, "substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

The efficacy of treating Parkinson's disease using methods and compositions of the present invention may be assessed by various methods. For example, efficacy may be assessed by monitoring and assessing the motor symptoms of the disease, including tremor, bradykinesia, rigidity of limb and muscle tone, postural instability. Additionally, efficacy may be assessed by monitoring for improvements in neuropsychiatric symptoms which include, for example, speech, cognition, mood, behavior, and thought.

In various embodiments, the present methods show an improvement in disease symptoms as measured by the Unified Parkinson's Disease Rating Scale as described in Movement Disorders Vol. 23, No. 15, 2008, pp. 2129-2170, which is incorporated herein by reference in its entirety.

In various embodiments, the present methods show an improvement in disease symptoms as measured by the MDS-UPDRS Movement Disorders. 22 (1): 41-47, which is incorporated herein by reference in its entirety. In various embodiments, the present methods show improvement in the following scales and subscales: (1) nonmotor experiences of daily living, (2) motor experiences of daily living, (3) motor examination, and (4) motor complications (e.g., each subscale rating is reduced towards normal (e.g., 4 to 0, or 4 to 1, or 4 to 2, or 4 to 3, or 3 to 0, or 3 to 1, or 3 to 2, or 2 to 1, or 2 to 0, or 1 to 0, where 0=normal, 1=slight, 2=mild, 3=moderate, and 4=severe).

In various embodiments, the present methods pertain to the use of polyvalent derivatives of emoxypine. In various embodiments, the compound is a poly-imino or poly-amido emoxypine derivative. In various embodiments, the poly-imino or poly-amido emoxypine derivative is a compound of Formula I or Formula II:

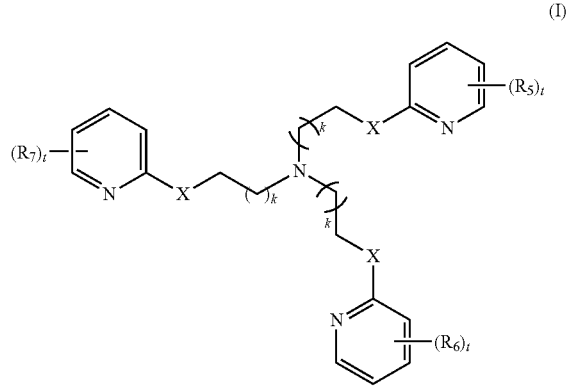

(I)

wherein:
X is —NH—C(=O)— or —CH(=N)—;
each R₅, R₆, or R₇ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;
each t is independently 0, 1, 2, 3, 4, or 5;
each k is independently 0, 1, 2, 3, 4, 5, or 6,

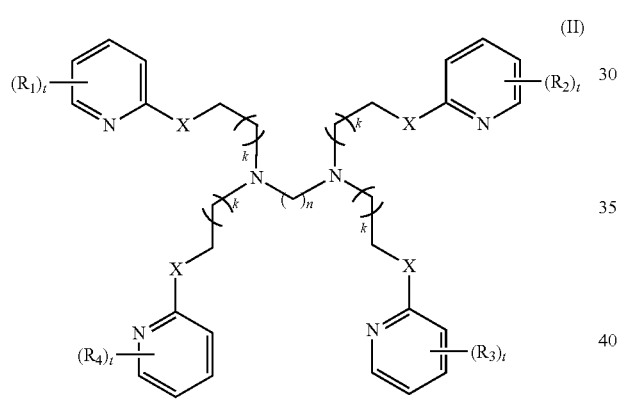

(II)

wherein:
X is —NH—C(=O)— or —CH(=N)—;
each R₁, R₂, R₃, or R₄ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;
n is 2, 3, 4, 5, 6, 7, 8, 9, 10, 11, 12, 13, 14, or 15;
each t is independently 0, 1, 2, 3, 4, or 5;
each k is independently 0, 1, 2, 3, 4, 5, or 6.

In further embodiments, the compound is tri imino-emoxypine (also known as "MHP-tren triimine"), tetra imino-emoxypine, or a poly-amido emoxypine derivative.

In some embodiments, the compound is:

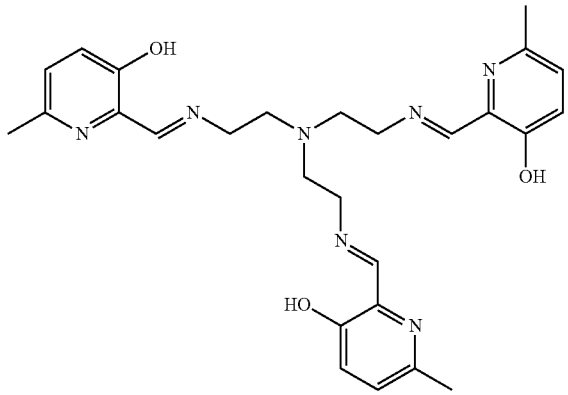 [SMILES: Cc1ccc(O)c(/C=N/CCN(CC/N=C/c2nc(C)ccc2O)CC/N=C/c2nc(C)ccc2O)n1]

In some embodiments, the compound is:

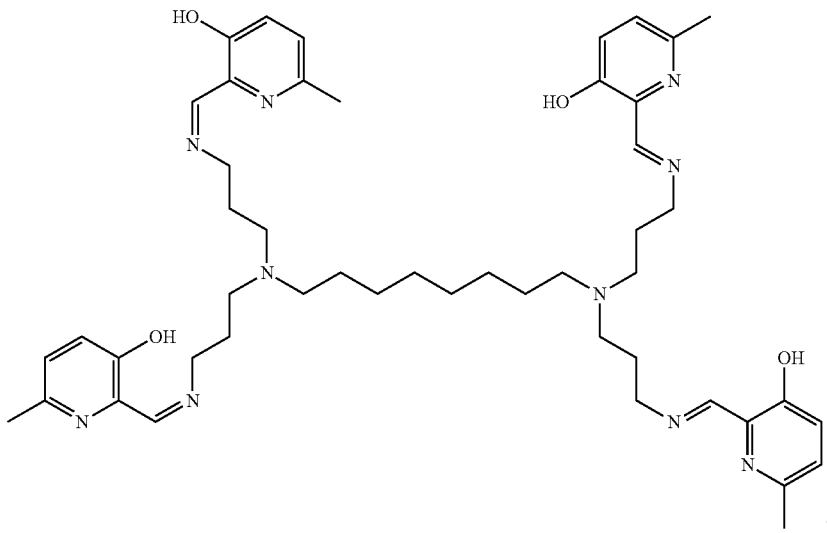 [SMILES: Cc1ccc(O)c(/C=N\CCCN(CCCCCCCCN(CCC/N=C/c2nc(C)ccc2O)CCC/N=C/c2nc(C)ccc2O)CCC/N=C\c2nc(C)ccc2O)n1]

In some embodiments, the compound is:

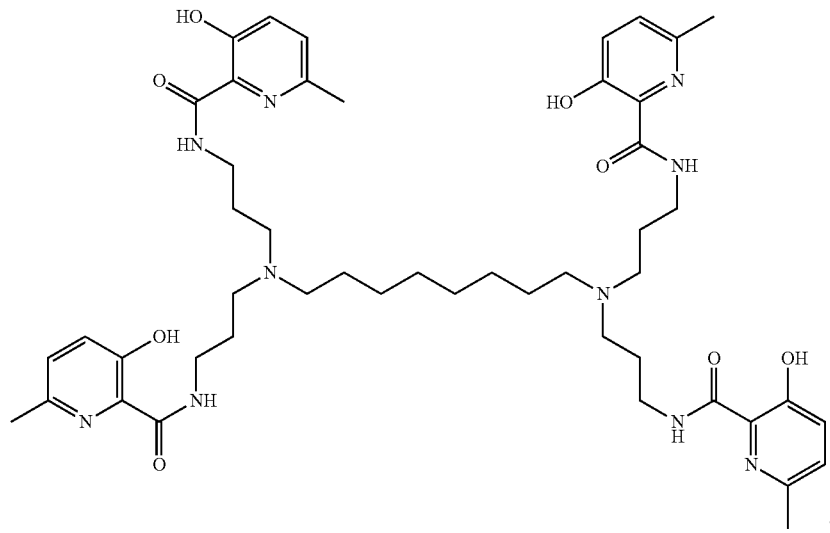 [SMILES: Cc1ccc(O)c(C(=O)NCCCN(CCCCCCCCN(CCCNC(=O)c2nc(C)ccc2O)CCCNC(=O)c2nc(C)ccc2O)CCCNC(=O)c2nc(C)ccc2O)n1]

In various embodiments, the present methods pertain to the use of polyvalent derivatives of emoxypine (e.g., poly-imino or poly-amido emoxypine derivatives) or a related compound for the present treatments or preventions. In some embodiments, the present methods pertain to use of a compound of Formula I or Formula II:

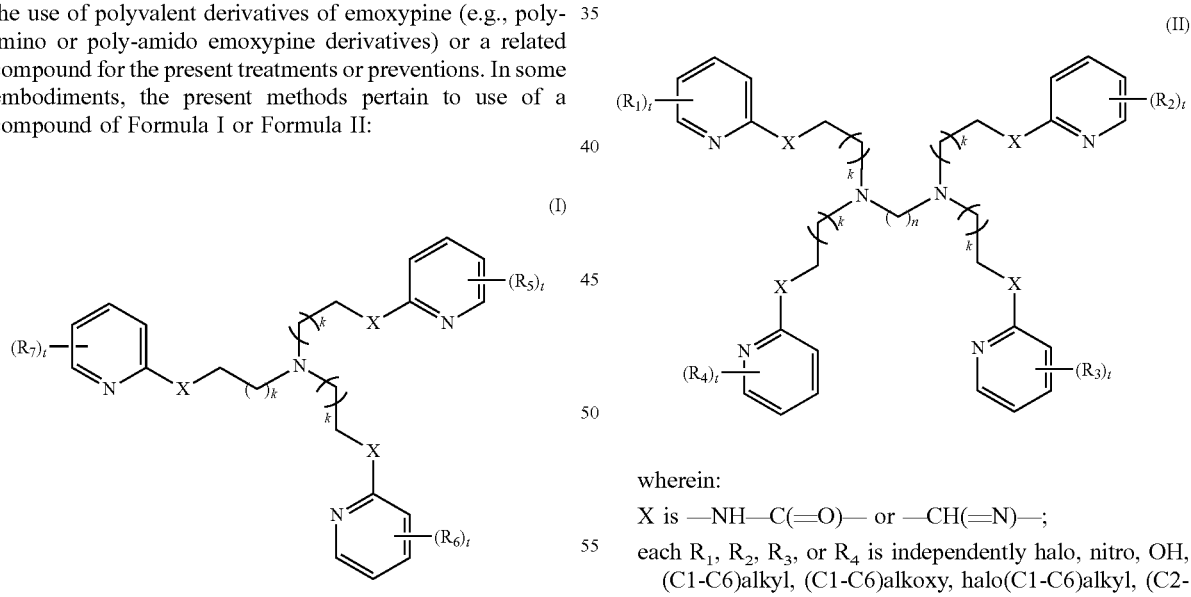

wherein:

X is —NH—C(=O)— or —CH(=N)—;

each $R_5$, $R_6$, or $R_7$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;

each t is independently 0, 1, 2, 3, 4, or 5;

each k is independently 0, 1, 2, 3, 4, 5, or 6, wherein:

X is —NH—C(=O)— or —CH(=N)—;

each $R_1$, $R_2$, $R_3$, or $R_4$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;

n is 2, 3, 4, 5, 6, 7, 8, 9, 10, 11, 12, 13, 14, or 15;

each t is independently 0, 1, 2, 3, 4, or 5;

each k is independently 0, 1, 2, 3, 4, 5, or 6.

In some embodiments, the present methods pertain to the use of tri imino-emoxypine, tetra imino-emoxypine, or a poly-amido emoxypine or a related compound for the present treatments or preventions.

In various embodiments, present methods pertain to the use of:
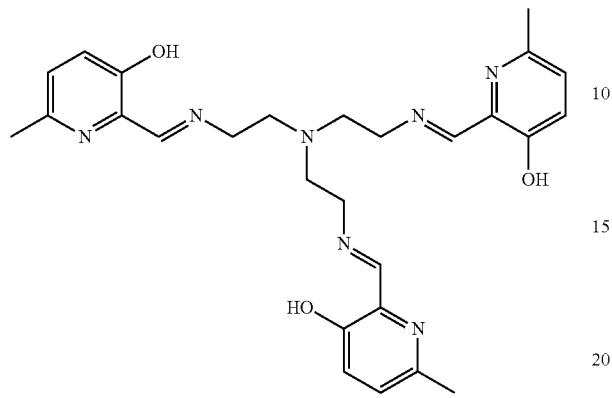
for the present treatments or preventions.
In various embodiments, present methods pertain to the use of:
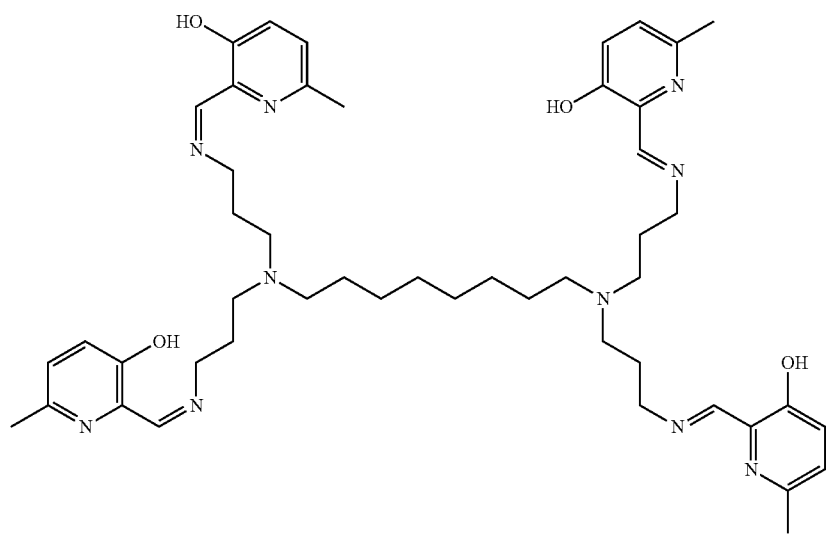 [SMILES: Cc1ccc(O)c(/C=N\CCCN(CCCCCCCCN(CCC/N=C/c2nc(C)ccc2O)CCC/N=C/c2nc(C)ccc2O)CCC/N=C\c2nc(C)ccc2O)n1]
for the present treatments or preventions.

In various embodiments, present methods pertain to the use of:

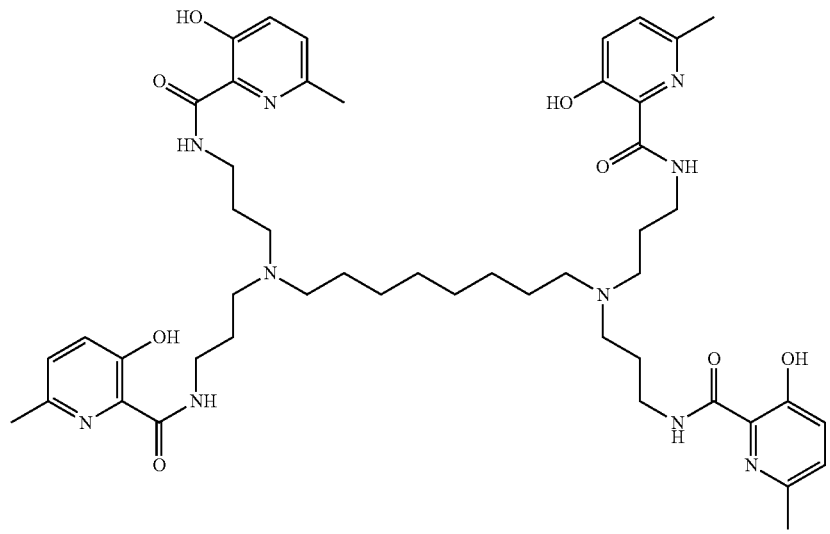 [SMILES: Cc1ccc(O)c(C(=O)NCCCN(CCCCCCCCN(CCCNC(=O)c2nc(C)ccc2O)CCCNC(=O)c2nc(C)ccc2O)CCCNC(=O)c2nc(C)ccc2O)n1]

for the present treatments or preventions.

In some embodiments, the present invention contemplates use of a compound of Formula I or Formula II for the preparation of a medicament for the treatment of a synucleinopathy,

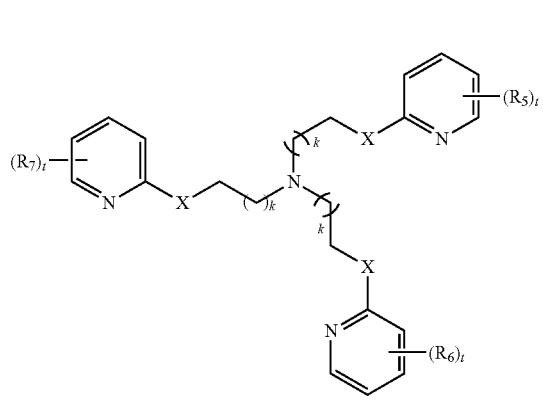
(I)

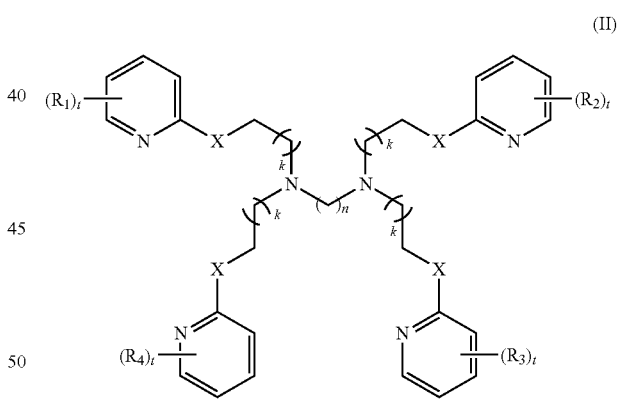
(II)

wherein:
X is —NH—C(=O)— or —CH(=N)—;
each $R_5$, $R_6$, or $R_7$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;
each t is independently 0, 1, 2, 3, 4, or 5;
each k is independently 0, 1, 2, 3, 4, 5, or 6, or wherein:
X is —NH—C(=O)— or —CH(=N)—;
each $R_1$, $R_2$, $R_3$, or $R_4$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;
n is 2, 3, 4, 5, 6, 7, 8, 9, 10, 11, 12, 13, 14, or 15;
each t is independently 0, 1, 2, 3, 4, or 5;
each k is independently 0, 1, 2, 3, 4, 5, or 6.
wherein the treatment comprises disaggregation of α-synuclein.

In some embodiments, the present invention contemplates the use of the compound having the structure of:

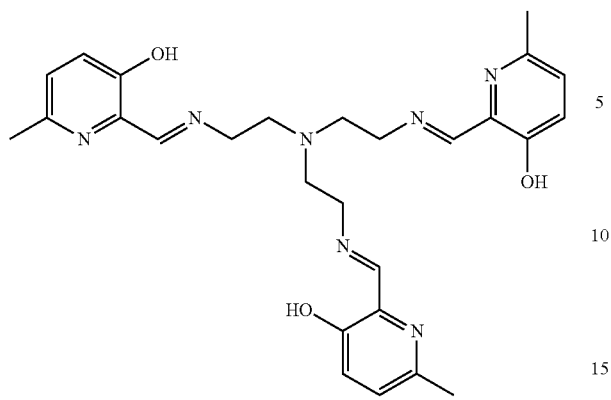
for the preparation of a medicament for the treatment of a synucleinopathy, wherein the treatment comprises disaggregation of α-synuclein.
In some embodiments, the present invention contemplates the use of the compound having the structure of:
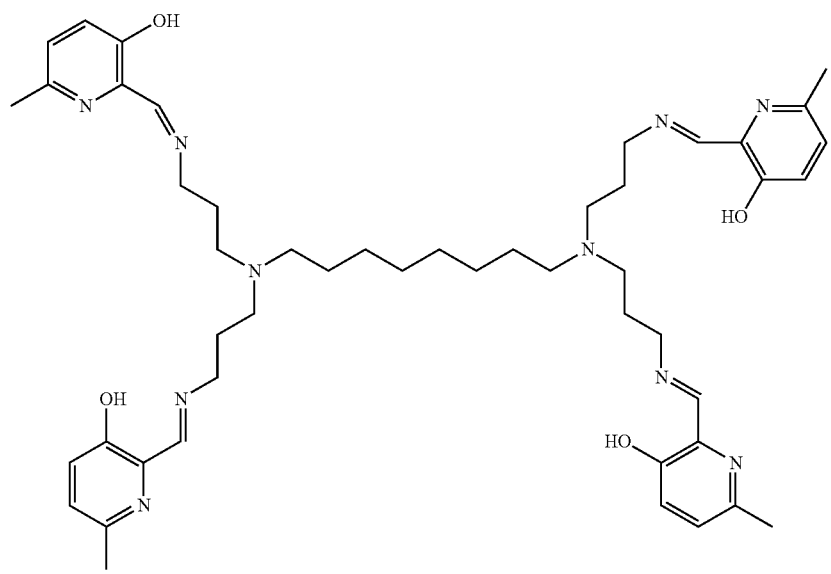

for the preparation of a medicament for the treatment of a synucleinopathy, wherein the treatment comprises disaggregation of α-synuclein.

In some embodiments, the present invention contemplates the use of the compound having the structure of:

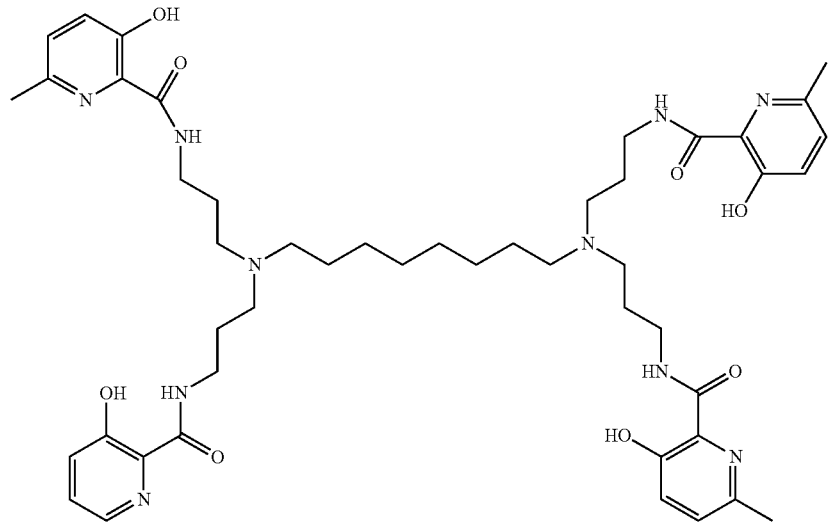

for the preparation of a medicament for the treatment of a synucleinopathy, wherein the treatment comprises disaggregation of α-synuclein.

In various embodiments, the present invention contemplates a method for treating or preventing a synucleinopathy, comprising administering to a subject in need thereof an effective amount of a compound of Formula I:

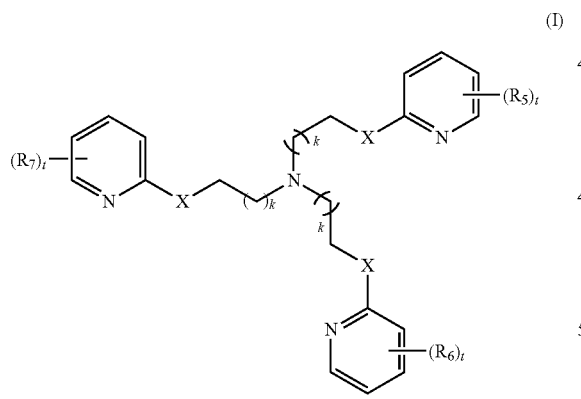

wherein:

X is —NH—C(=O)— or —CH(=N)—;

each $R_5$, $R_6$, or $R_7$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;

each t is independently 0, 1, 2, 3, 4, or 5;

each k is independently 0, 1, 2, 3, 4, 5, or 6.

In some embodiments, the present invention contemplates a method for treating or preventing a synucleinopathy, comprising administering an effective amount of a compound to a subject in need thereof, wherein the compound is:

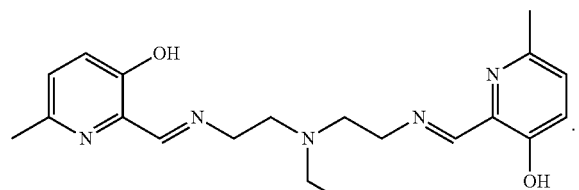

In various embodiments, the present invention contemplates a method for treating or preventing a synucleinopathy, comprising administering to a subject in need thereof an effective amount of a compound of Formula II:

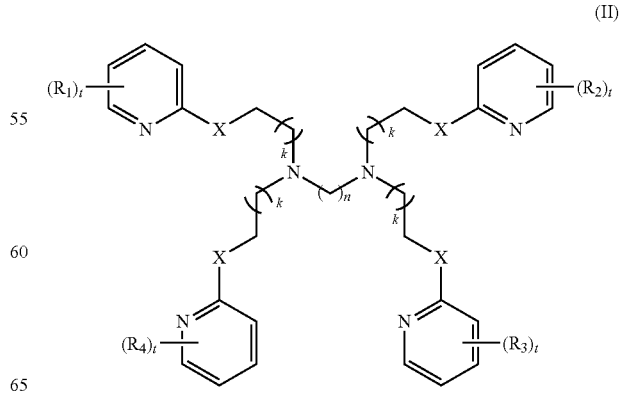

wherein:

X is —NH—C(=O)— or —CH(=N)—;

each $R_1$, $R_2$, $R_3$, or $R_4$ is independently halo, nitro, OH, (C1-C6)alkyl, (C1-C6)alkoxy, halo(C1-C6)alkyl, (C2-C6)alkenyl, (C3-C8)cycloalkyl, (C2-C8) heterocyclo, aryl, or heteroaryl;

n is 2, 3, 4, 5, 6, 7, 8, 9, 10, 11, 12, 13, 14, or 15;

each t is independently 0, 1, 2, 3, 4, or 5;

each k is independently 0, 1, 2, 3, 4, 5, or 6.

In some embodiments, the present invention contemplates a method for treating or preventing a synucleinopathy, comprising administering an effective amount of a compound to a subject in need thereof, wherein the compound is:

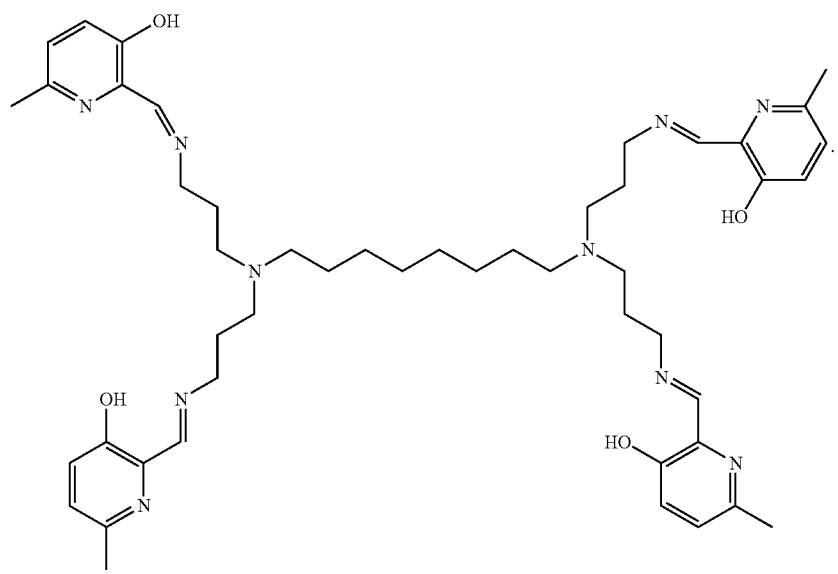

In some embodiments, the present invention contemplates a method for treating or preventing a synucleinopathy, comprising administering an effective amount of a compound to a subject in need thereof, wherein the compound is:

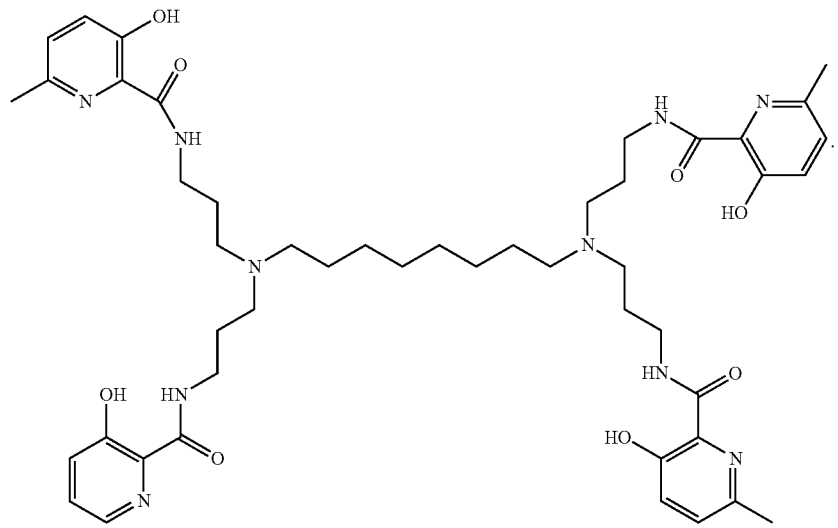

In various embodiments, the present methods pertain to the use of emoxypine or a related compound for the present treatments or preventions.

In various embodiments, the present methods pertain to the use of methyl 3-hydroxy-6-methyl picolinate (MHP ester) or a related compound for the present treatments or preventions.

In various embodiments, acids and salts of the compounds described herein are provided. In some embodiments, a compound described herein is an anion. The counterpart species may be a counterion and the combination of a compound described herein with a counterion is an acid or salt. Counter ions of a compound described herein may include, but are not limited to, cationic hydrogen species including protons; monovalent inorganic cations including lithium, sodium, and potassium; divalent inorganic cations including magnesium, calcium, manganese, zinc, copper and iron; polyvalent inorganic cations including iron; quaternary nitrogen species including ammonium, cycloheptyl ammonium, cyclooctyl ammonium, N,N-dimethylcyclohexyl ammonium, and other organic ammonium cations; sulfonium species including triethylsulfonium and other organic sulfonium compounds; organic cations including pyridinium, piperidinium, piperazinium, quinuclidinium, pyrrolium, tripiperazinium, and other organic cations; polymeric cations including oligomers, polymers, peptides, proteins, positively charged ionomers, and other macromolecular species that possess sulfonium, quaternary nitrogen and/or charged organometallic species in pendant groups, chain ends, and/or the backbone of the polymer.

The invention is not limited to pairings that are purely ionic; indeed, it is known in the art that paired ions may evidence some degree of covalent or coordinate bond characteristic between the two components of the pair. The compounds of the invention may comprise a single type of counterion or may contain mixed counterions, and may optionally contain a mixture of anions of which a compound of a polyvalent derivative of emoxypine is one. The compositions may optionally include crown ethers, cryptands, and other species capable of chelating or otherwise complexing the counterions. The compounds of the invention may likewise optionally include acidic macrocycles or other species that are capable of complexing the compounds of the invention through hydrogen bonds or other molecular attractions.

In some embodiments, the compounds described herein include derivatives that are modified, i.e., by the covalent attachment of any type of molecule to the compound such that covalent attachment does not prevent the activity of the compound. For example, but not by way of limitation, derivatives include compounds that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, or formylation. Additionally, the derivatives can contain one or more non-classical amino acids.

In still other embodiments, the compounds described herein may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and a targeting agent.

In yet other embodiments, the present invention provides for the compounds described herein and pharmaceutically acceptable esters, prodrugs, salts, solvates, enantiomers, stereoisomers, active metabolites, co-crystals, and other physiologically functional derivatives thereof.

In an embodiment, the compound described herein is in the form of a pharmaceutically acceptable salt, namely those salts which are suitable for use in contact with the tissues of humans and other animals without undue toxicity, irritation, allergic response and the like, and are commensurate with a reasonable benefit/risk ratio. Pharmaceutically acceptable salts are well known in the art. The salts can be prepared in situ during the final isolation and purification of the compound, or separately by reacting the free base function with a suitable acid or a free acid functionality with an appropriate alkaline moiety. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The compounds described herein, or their pharmaceutically acceptable salts which are used in accordance with the present invention, may exhibit stereoisomerism by virtue of the presence of one or more asymmetric or chiral centers in the compounds. The present invention contemplates the various stereoisomers and mixtures thereof. Desired enantiomers can be obtained by chiral synthesis from commercially available chiral starting materials by methods well known in the art, or may be obtained from mixtures of the enantiomers by resolution using known techniques.

Solvate as used herein refers to a pharmaceutically acceptable solvate form of an agent that retains the biological effectiveness of such agent. Examples of solvates include a compound of the present invention in combination with, for example, water, isopropanol, ethanol, methanol, DMSO, ethyl acetate, acetic acid, or ethanolamine.

Prodrug, as used herein refers to an agent that is converted under physiological conditions or by solvolysis or metabolically (e.g., in vivo) to a specified agent that is pharmaceutically active.

Active metabolite, as used herein refers to a pharmacologically active product produced through metabolism in the body of a specified agent.

Co-crystal as used herein refers to a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates.

In one aspect, the present invention provides a compounds described herein, and a pharmaceutically acceptable carrier or excipient. The pharmaceutical composition can be in any suitable form appropriate for the desired use and route of administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable pharmaceutical excipients are described in Remington's Pharmaceutical Sciences 1447-1676 (Alfonso R. Gennaro eds., 19th ed. 1995), incorporated herein by reference.

Additionally, the pharmaceutical compositions of the present invention may contain adjuvants such as preservatives, wetting agents, emulsifying agents, pH buffering agents, and dispersing agents. Further, auxiliary, stabilizing, thickening, lubricating, and coloring agents can be included. Prevention of the action of microorganisms may be ensured by the inclusion of various antibacterial and antifungal agents, for example, paraben, chlorobutanol, phenol sorbic acid, and the like. The pharmaceutical compositions may also include isotonic agents such as sugars, sodium chloride, and the like.

Where necessary, the pharmaceutical compositions can also include a solubilizing agent. Also, the agents can be delivered with a suitable vehicle or delivery device as known in the art. Compositions for administration can optionally include a local anesthetic such as, for example, lidocaine to lessen pain at the site of the injection.

The pharmaceutical compositions of the present invention can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In one embodiment, the pharmaceutical composition is in the form of a capsule. In another embodiment, the pharmaceutical composition is in the form of a tablet.

In some embodiments, the administration of any of the described compounds is any one of oral, intravenous, and parenteral. In various embodiments, routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically, for example, to the ears, nose, eyes, or skin. In some embodiments, the administering is effected orally or by parenteral injection. The mode of administration can be left to the discretion of the practitioner, and depends in-part upon the site of the medical condition. In various embodiments, administration results in the release of any agent described herein into the bloodstream.

Any compound and/or pharmaceutical composition described herein can be administered orally. Such compounds and/or pharmaceutical compositions can also be administered by any other convenient route, for example, by intravenous infusion or bolus injection, by absorption through epithelial or mucocutaneous linings (e.g., oral mucosa, rectal and intestinal mucosa, etc.) and can be administered together with an additional therapeutic agent. Administration can be systemic or local. In some embodiments, administration is not at the site of infection to avoid, for example, hydrolysis of the compound at the site of infection. Various delivery systems are known, e.g., encapsulation in liposomes, microparticles, microcapsules, capsules, etc., and can be used. In specific embodiments, it may be desirable to administer locally to the area in need of treatment.

In various embodiments, a compound of the present invention is formulated as described in WO 2006/102748, which is incorporated herein by reference in its entirety.

In one embodiment, a compound described herein and/or pharmaceutical composition described herein is formulated in accordance with routine procedures as a composition adapted for oral administration to humans. Solid dosage forms for oral administration include, for example, capsules, tablets, pills, powders, and granules. In such dosage forms, the active compound is mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Non-limiting examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Dosage forms suitable for parenteral administration (e.g., intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents known in the art. Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions, and by the use of surfactants.

Any compound described herein and/or pharmaceutical composition described herein can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, Eudragit, other polymer matrices, gels, permeable membranes, osmotic systems, multilayer coatings, microparticles, liposomes, microspheres, or a combination thereof to provide the desired release profile in varying proportions. Suitable controlled- or sustained-release formulations can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Formulations comprising the compounds described herein and/or pharmaceutical compositions of the present invention may conveniently be presented in unit dosage forms and may be prepared by any of the methods known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

It will be appreciated that the actual dose of the compounds described herein and/or pharmaceutical compositions of the present invention to be administered according to the present invention may vary according to the particular compound, the particular dosage form, and the mode of administration. Many factors that may modify the action of the inositpresent agents (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the compounds described herein and/or pharmaceutical compositions of the present invention can be administered in unit dosage forms (e.g., tablets or capsules) containing, for example, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, or from about 0.1 mg to about 1 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In some embodiments, the compounds described herein and/or pharmaceutical compositions of the present invention are administered at an amount of from about 0.01 mg to about 1,000 mg daily, from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, or from about 0.1 mg to about 1 mg daily.

In various embodiments, the compounds described herein and/or pharmaceutical compositions of the present invention are administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In some embodiments, a suitable dosage of the compounds described herein and/or pharmaceutical compositions of the present invention is in a range of about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween. In other embodiments, a suitable dosage of a compound of Formula I, Ia, or Ib (e.g. pyridoxal phosphate, emoxypine, methyl 3-hydroxy-6-methyl picolinate (MHP ester) or a related compound) is in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the compounds and/or pharmaceutical compositions described herein may be administered, for example, more than once daily, about once per day, about every other day, about every third day, about once a week, about once every two weeks, about once every month, about once every two months, about once every three months, about once every six months, or about once every year.

Administration of the present compounds may be combined with one or more additional therapeutic agents (e.g., 1, or 2, or 3, or 4, or 5 additional therapeutic agents). Such combinations may lead to synergism and/or additive and/or potent effects at a lower dose of the present compounds and/or the one or more additional therapeutic agents. Co-administration of the present compounds and the additional therapeutic agent may be simultaneous or sequential. Further the pharmaceutical compositions including the present compounds may comprise the additional therapeutic agent (e.g., via co-formulation). Further, in some embodiments, the present compounds may be administered to a patient that is undergoing treatment with one or more additional therapeutic agent. Further, in some embodiments, the present compounds may supplant a patient's current treatment with one or more additional therapeutic agent.

In one embodiment, the additional therapeutic agent and the present compounds are administered to a subject simultaneously. The term "simultaneously" as used herein, means that the additional therapeutic agent and the present compounds are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and present compounds can be by simultaneous administration of a single formulation (e.g., a formulation comprising the additional therapeutic agent and the present compounds) or of separate formulations (e.g., a first formulation including the additional therapeutic agent and a second formulation including the present compounds).

Co-administration does not require the additional therapeutic agent to be administered simultaneously, if the timing of their administration is such that the pharmacological activities of the additional therapeutic agent and the present compounds overlap in time, thereby exerting a combined therapeutic effect. For example, the additional therapeutic agent and the present compounds can be administered sequentially. The term "sequentially" as used herein means that the additional therapeutic agent and the present compounds are administered with a time separation of more than about 60 minutes. For example, the time between the sequential administration of the additional therapeutic agent and the present compounds can be more than about 60 minutes, more than about 2 hours, more than about 5 hours, more than about 10 hours, more than about 1 day, more than about 2 days, more than about 3 days, or more than about 1 week apart. The optimal administration times may depend on the rates of metabolism, excretion, and/or the pharmacodynamic activity of the additional therapeutic agent and the present compounds being administered. Either the additional therapeutic agent or the present compound may be administered first.

Co-administration also does not require the additional therapeutic agents to be administered to the subject by the same route of administration. Rather, each therapeutic agent can be administered by any appropriate route, for example, parenterally or non-parenterally.

In various embodiments, the additional therapeutic agent is a Parkinson's disease treatment agent. For example, in various embodiments, the Parkinson's disease treatment agent is optionally selected from one or more of levodopa (for example, in combination with tolcapone, entacapone, carbidopa, or benserazide), dopamine agonists as described herein (for example, apomorphine, bromocriptine, pergolide, pramipexole, ropinirole, piribedil, cabergoline, apomorphine and lisuride), MAO-B inhibitors as described herein (for example, deprenyls such as selegiline and rasagiline), Piribedil, pramipexole (e.g., MIRAPEX, MIRAPEXIN, SIFROL), bromocriptine (e.g., PARLODEL, CYCLOSET, BROTIN), Ropinirole (e.g., REQUIP, REPREVE, RONIROL, ADARTREL), sumanirole (e.g. PNU-95,666), aplindore (e.g., DAB-452), amantadine, anticholinergics (for example, artane, Cogentin), quetiapine, cholinesterase inhibitors, modafinil, tyrosine hydroxylase, N-phenyl-7-(hydroxylimino)cyclopropa[b]chromen-1a-carboxamide (PHCCC), and non-steroidal anti-inflammatory drugs.

In various embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient or a subject. In some embodiments, the human is a female. In some embodiments, the human is a male.

The invention provides kits that can simplify the administration of the compounds and/or pharmaceutical compositions described herein. The kit is an assemblage of materials or components, including at least one of the formulations described herein. The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to affect a desired outcome, such as to treat, for example, Parkinson's disease. Optionally, the kit also contains other useful components, such as, diluents, buffers, pharmaceutically acceptable carriers, syringes, catheters, applicators, pipetting or measuring tools, bandaging materials or other useful paraphernalia as may be readily recognized by those of skill in the art.

The materials and components assembled in the kit can be provided to the practitioner store in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

This invention is further illustrated by the following non-limiting examples.

EXAMPLES

Example 1: Experiments Related to the α-Synuclein Disaggregation with Tetra Imino-Emoxypine Disaggregation of α-Synuclein with Tetra Imino-Emoxypine.

Assays measuring activity of tetra imino-emoxypine for dissolution of alpha-synuclein aggregates are performed.

Example 2: Synthesis of Tetra Imino-Emoxypine Derivative and a Poly-Amido Emoxypine Derivative The poly-amido emoxypine derivative and the tetra imino-emoxypine derivative of the present invention are synthesized through the following modes of formation, respectively:

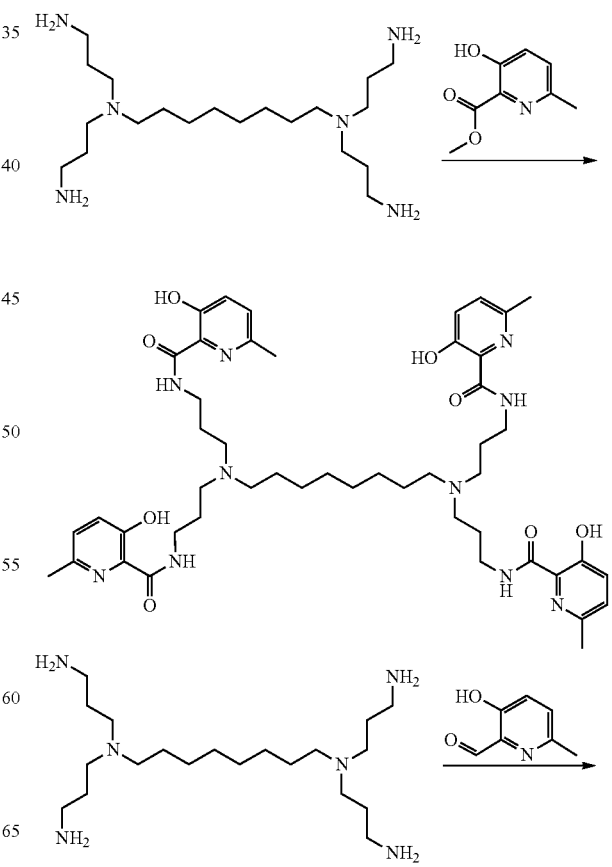

-continued

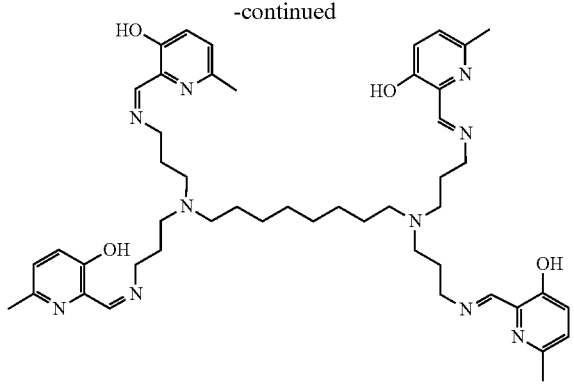

Example 3: Synthesis of Tri Imino-Emoxypine Derivative

The tri imino-emoxypine (also known as MHP-tren triimine) derivative of the present invention is synthesized through the following mode of formation:

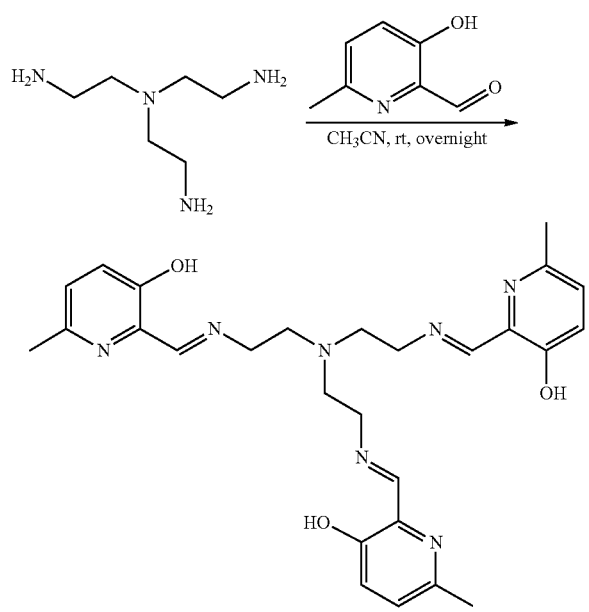

Example 4: Alpha-Synuclein Disaggregation with Tri Imino-Emoxypine (Also Known as "MHP-Tren Triimine")

Disaggregation of α-synuclein fibrils using MHP-tren triimine (i.e., tri imino-emoxypine) was studied. The ratio of MHP-tren triimine:α-synuclein was 70 (r70).

Figure 2:
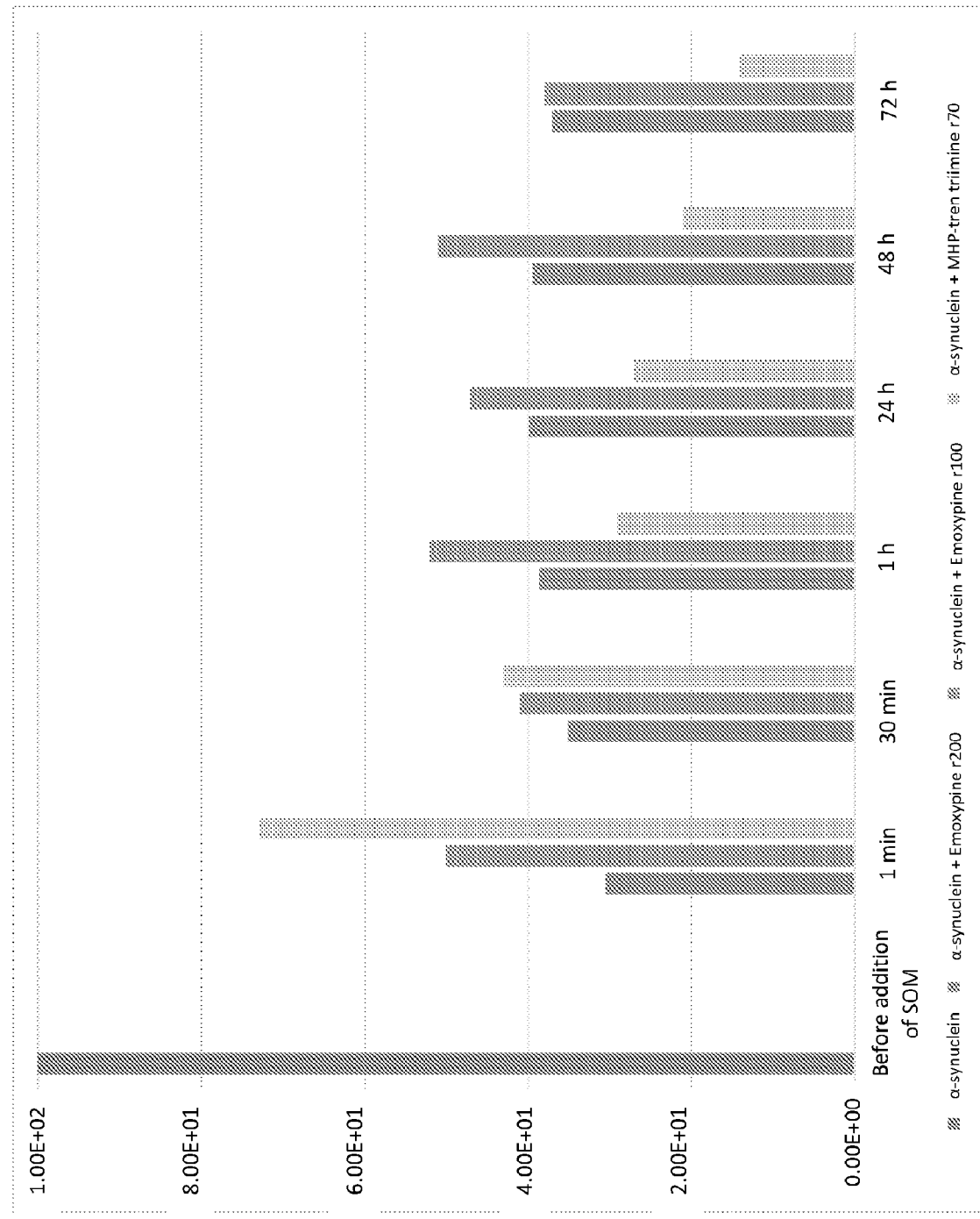
FIG. 2 depicts emission intensity of ThT at 482 nm (λexc=450 nm), in the presence of α-synuclein amyloids fibrils, using Emoxypine r200, Emoxypine r100, MHP-tren triimine (also known as tri imino-emoxypine) r70 (light blue trace and yellow trace, respectively) from 1 minute to 3 days (72 h), where the bars from left to right in each set of histograms represents: α-synuclein+Emoxypine r200; α-synuclein+Emoxypine r100; and α-synuclein+MHP tren-triimine r70, respectively. The far leftmost bar of the graph, titled "Before addition of SOM" represents a sample without emoxypine or MHP tren-triimine, i.e. with 100% of α-synuclein aggregates left.

Fluorescence measurements were performed by comparing the emission of thiovlavin T (ThT) in the presence of aggregates, without and with MHP-tren triimine at different times after the addition of MHP-tren triimine, from one minute to several days (λ emission of interest=482 nm, λ excitation=450 nm). Fluorescent measurements were also performed by comparing the emission of thiovlavin T (ThT) in the presence of aggregates and either emoxypine or MHP-tren triimine. The results (see, FIG. 1A-1B, FIG. 2 and Tables 1-2, below) show higher solubilization percentages using MHP-tren triimine as compared to emoxypine. Interestingly, MHP-tren triimine exhibited a slow effect (e.g., 27% of solubilization after 1 min), yet the solubilization degree of MHP-tren triimine constantly increased and finally reached 86% after 3 days. The long-term efficiency of the triimine molecule is therefore better than that of its triamide analogue.

TABLE 1

Percentage of solubilization along the time using MHP-tren triimine (i.e., tri imino-emoxypine) at r70, from 1 minute to 3 days (72 h).

| Time | Percentage of solubilization |
|---|---|
| 1 min | 27.0 |
| 30 min | 47.1 |
| 1 h | 71.0 |
| 24 h | 72.8 |
| 48 h | 79.5 |
| 72 h | 86.1 |

TABLE 2

Percentage of solubilization along the time using Emoxypine r200, Emoxypine r100, MHP-tren triimine r70, from 1 minute to 3 days (72 h).

| Time | Percent of Solubilization of Emoxypine r200 | Percent of Solubilization of Emoxypine r100 | Percent of Solubilization of MHP-tren triimine r70 |
|---|---|---|---|
| 1 min | 69 | 50 | 27 |
| 30 min | 65 | 59 | 57 |
| 1 h | 61 | 48 | 71 |
| 24 h | 60 | 53 | 73 |
| 48 h | 61 | 49 | 79 |
| 72 h | 63 | 62 | 86 |

Figure 3:
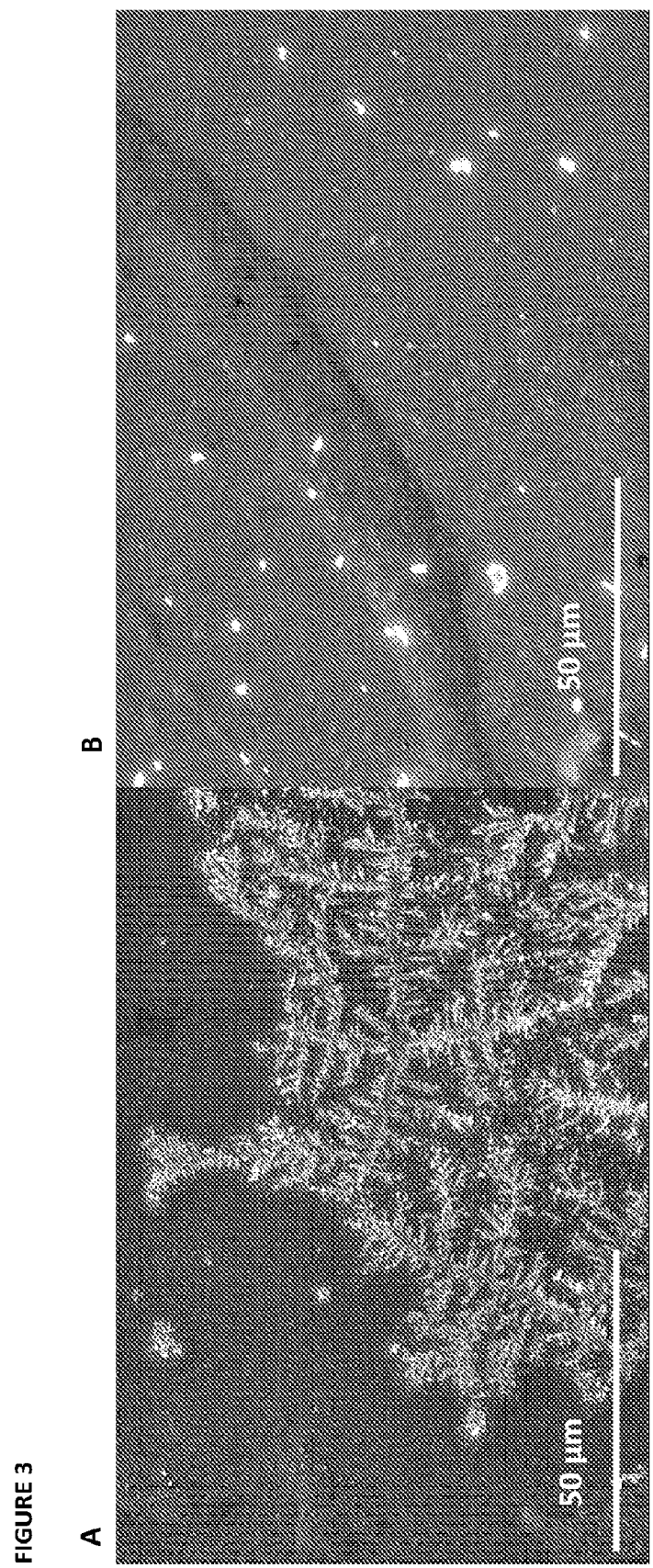
FIG. 3A to FIG. 3B shows SEM images of α-synuclein fibrils without (FIG. 2A, left) and with (FIG. 2B, right) MHP-tren triimine.

Scanning electron microscope (SEM) images were also recorded, and the result shows that the sample without the triimine molecule shows "superaggregated" structures (FIG. 3A), while the sample with the triimine molecule displays no apparent fiber or big aggregates-only small dots are visible, most likely referring to α-synuclein monomers (FIG. 3B).

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for treating or preventing a synucleinopathy, comprising administering to a subject in need thereof an effective amount of a compound of Formula I:

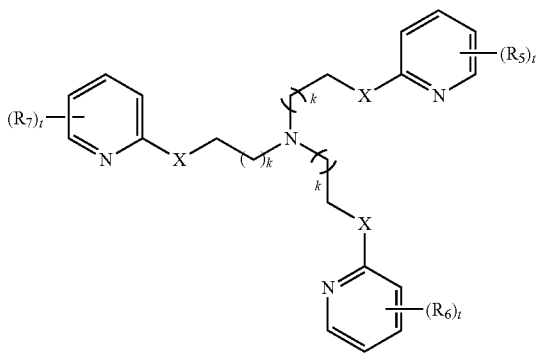

wherein:
X is —NH—C(=O)— or —CH(=N)—;
each $R_5$, $R_6$, or $R_7$ is independently halo, nitro, OH, (C1-C6) alkyl, (C1-C6) alkoxy, halo (C1-C6) alkyl, (C2-C6) alkenyl, (C3-C8) cycloalkyl, (C2-C8) heterocyclo, aryl, or heteroaryl;
each t is independently 0, 1, 2, 3, 4, or 5;
each k is independently 0, 1, 2, 3, 4, 5, or 6 and
wherein the synucleinopathy is a condition characterized by Lewy bodies; or a compound of Formula II:

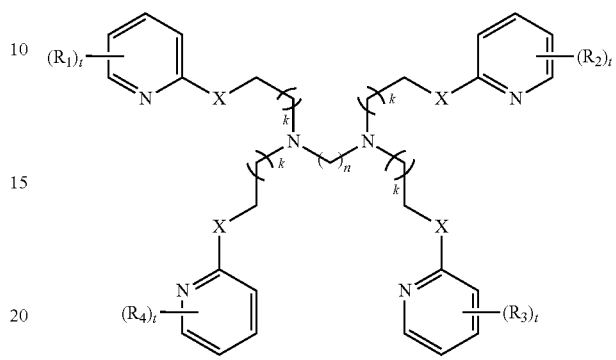

wherein:
X is —NH—C(=O)— or —CH(=N)—;
each $R_1$, $R_2$, $R_3$, or $R_4$ is independently halo, nitro, OH, (C1-C6) alkyl, (C1-C6) alkoxy, halo (C1-C6) alkyl, (C2-C6) alkenyl, (C3-C8) cycloalkyl, (C2-C8) heterocyclo, aryl, or heteroaryl;
n is 2, 3, 4, 5, 6, 7, 8, 9, 10, 11, 12, 13, 14, or 15;
each t is independently 0, 1, 2, 3, 4, or 5;
each k is independently 0, 1, 2, 3, 4, 5, or 6, and
wherein the synucleinopathy is a condition characterized by Lewy bodies.

2. The method of claim 1, wherein the compound of Formula I has the structure of:

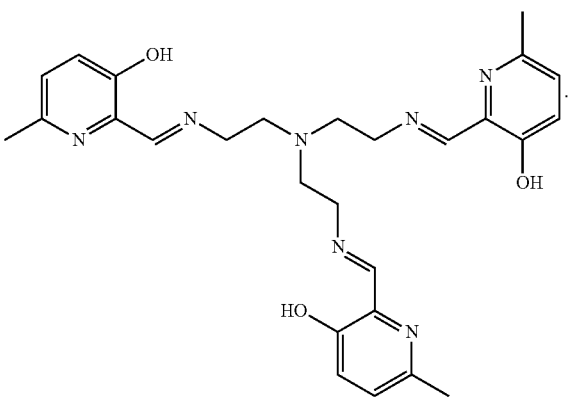 [SMILES: Cc1ccc(O)c(/C=N/CCN(CC/N=C/c2nc(C)ccc2O)CC/N=C/c2nc(C)ccc2O)n1]

3. The method of claim 1, wherein the compound of Formula II has the structure of:

4. The method of claim 1, wherein the compound of Formula II has the structure of:

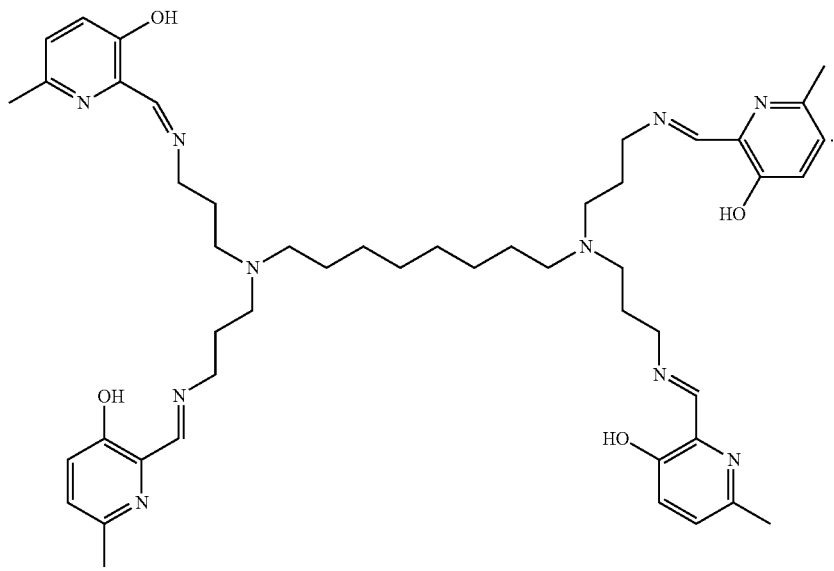

5. The method of claim 1, wherein the condition characterized by Lewy bodies is selected from Parkinson's disease, dementia with Lewy bodies, and multiple system atrophy.

6. The method of claim 5, wherein the Parkinson's disease is selected from Idiopathic Parkinson's disease, Vascular parkinsonism, drug-induced parkinsonism, dementia with Lewy bodies, Inherited Parkinson's, and Juvenile Parkinson's disease.

7. The method of claim 1, wherein the method results in disaggregation of α-synuclein and the disaggregation of α-synuclein comprises about a 20%, or about a 30%, or about a 40%, or about a 50%, or about a 60%, or about a 70%, or about a 80%, or about a 90%, or about a 95%, or about a 100% reduction in α-synuclein aggregation in the subject, relative to an untreated subject.

8. The method of claim 1, wherein the method does not substantially dissolve aggregates of beta-amyloid.

9. A method for the treatment of Parkinson's disease, comprising administering to a subject in need thereof an effective amount of a compound of Formula I:

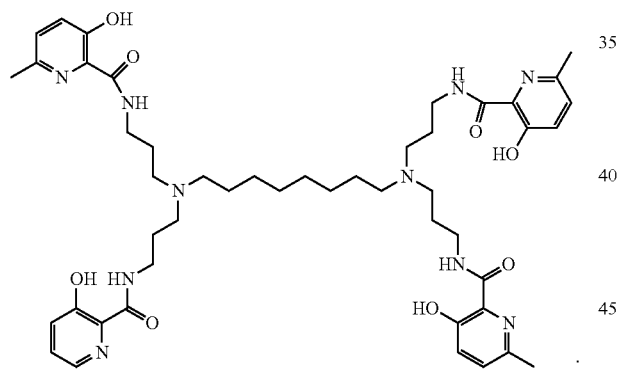

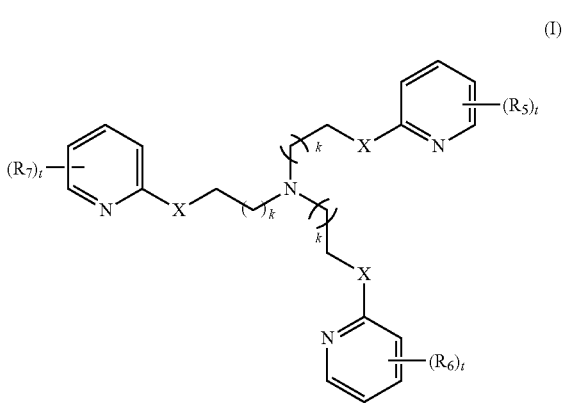

(I)

wherein:

X is —NH—C(=O)— or —CH(=N)—;

each $R_5$, $R_6$, or $R_7$ is independently halo, nitro, OH, (C1-C6) alkyl, (C1-C6) alkoxy, halo (C1-C6) alkyl, (C2-C6) alkenyl, (C3-C8) cycloalkyl, (C2-C8) heterocyclo, aryl, or heteroaryl;

each t is independently 0, 1, 2, 3, 4, or 5;

each k is independently 0, 1, 2, 3, 4, 5, or 6.

10. The method of claim 9, wherein the compound of Formula I has the structure of:
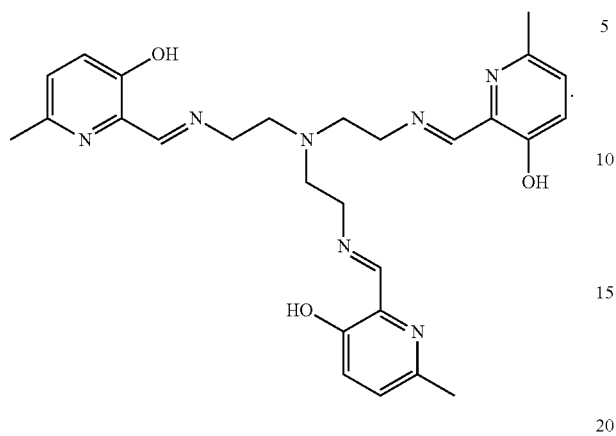
* * * * *